US005781640A

United States Patent [19]

Nicolino, Jr.

[11] Patent Number: 5,781,640

[45] Date of Patent: Jul. 14, 1998

[54] ADAPTIVE NOISE TRANSFORMATION SYSTEM

[76] Inventor: Sam J. Nicolino, Jr., 19784 Seagull Ct., Saratoga, Calif. 95070

[21] Appl. No.: 472,260

[22] Filed: Jun. 7, 1995

[51] Int. Cl.[6] .............................. H03B 29/00; A61F 11/06

[52] U.S. Cl. .................... 381/73.1; 381/71.13; 381/71.2; 381/94.1

[58] Field of Search ............................... 381/94, 71, 73.1, 381/110, 86; 415/119; 367/197, 198, 199

[56] References Cited

U.S. PATENT DOCUMENTS

| | | | |
|---|---|---|---|
| 4,771,472 | 9/1988 | Williams, IV et al. | 381/94 |
| 4,887,299 | 12/1989 | Cummins et al. | 381/68.4 |
| 4,914,706 | 4/1990 | Krause | 381/73.1 |
| 5,029,218 | 7/1991 | Nagayasu | 381/94 |
| 5,131,047 | 7/1992 | Hashimoto et al. | 381/71 |
| 5,179,747 | 1/1993 | Zink | 381/205 |
| 5,182,774 | 1/1993 | Bourk | 381/71 |
| 5,208,866 | 5/1993 | Kato et al. | 381/107 |
| 5,243,661 | 9/1993 | Ohkubo et al. | 381/94 |
| 5,293,578 | 3/1994 | Nagami et al. | 381/71 |
| 5,371,802 | 12/1994 | McDonald et al. | 381/71 |
| 5,406,149 | 4/1995 | An et al. | 327/311 |
| 5,452,274 | 9/1995 | Thompson | 367/197 |
| 5,455,779 | 10/1995 | Sato et al. | 381/73.1 |
| 5,559,891 | 9/1996 | Kuusama et al. | 381/71.8 |
| 5,689,572 | 11/1997 | Ohki et al. | 381/71.3 |

FOREIGN PATENT DOCUMENTS

| | | |
|---|---|---|
| 3-12698 | 1/1991 | Japan . |
| 2137791 | 11/1992 | United Kingdom . |

OTHER PUBLICATIONS

Elliott, S. J., and Nelson, P. A., "Active Noise Control", IEEE Signal Processing Magazine, Oct. 1993, pp. 12–35.

Maisel, James E., "Antinoise Makes Our World a Quieter Place", Personal Engineering & Instrumentation News, Aug. 1992, pp. 51–53.

Richards, Gary, "High–Tech Sound Wall on Horizon", San Jose Mercury News, Jun. 14, 1993.

Sanders, Robert, "Creating that Promised 'Quiet Ride'", The IEEE Grid, pp. 5–6.

*Primary Examiner*—Curtis A. Kuntz
*Assistant Examiner*—Xu Mei
*Attorney, Agent, or Firm*—Francis H. Lewis

[57] ABSTRACT

A system for suppressing the effects of undesirable noise from an annoying noise source contains a plurality of transformation sounds which, when combined with the noise form a sound that is pleasing to the ear. The transformation sounds are stored in the digital memory of the system or on a CD-ROM. The incident noise is detected and converted to signals which are dynamically analyzed, filtered and monitored to control the transformation sound selection process. The transformation sounds are modulated by a filtered signal derived from these noise signals that tracks the average energy in the noise. The transformation sounds include a primary transformation sound that is selected substantially continuously. The transformation sounds include also secondary transformation sounds that are selected for combination with the noise in periods when the primary transformation sound does not completely suppress the undesirable effects of the noise, and when the primary transformation sound is decreasing in volume. The system is especially effective in abating the traffic noise from freeways at nearby locations.

15 Claims, 4 Drawing Sheets

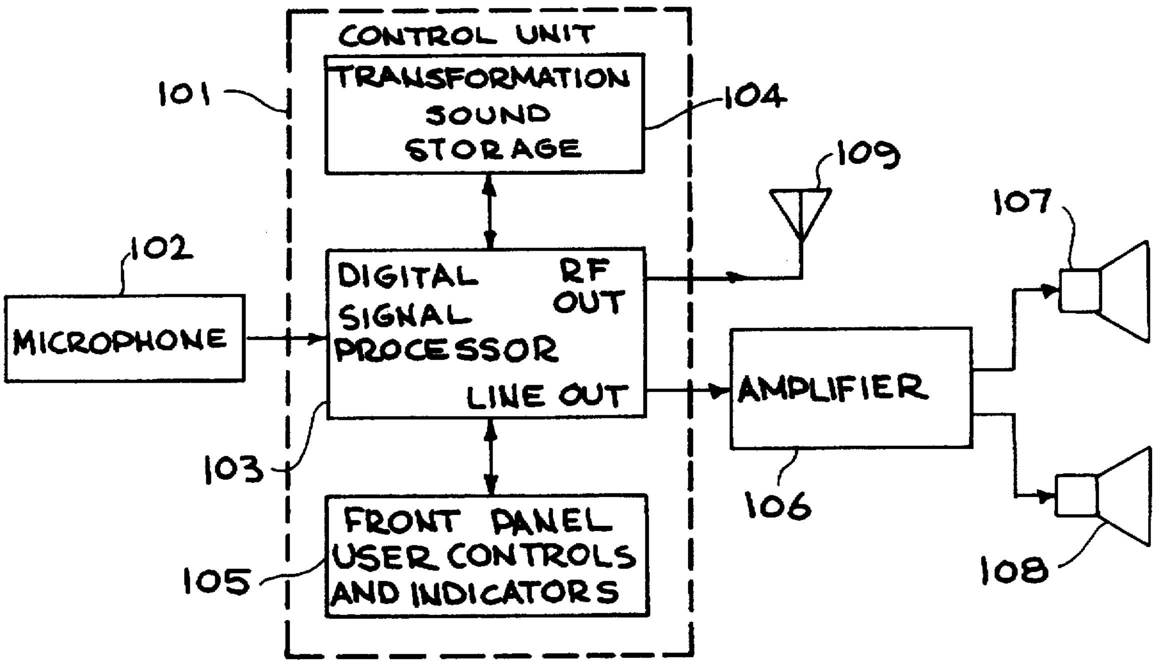
FIG. 1
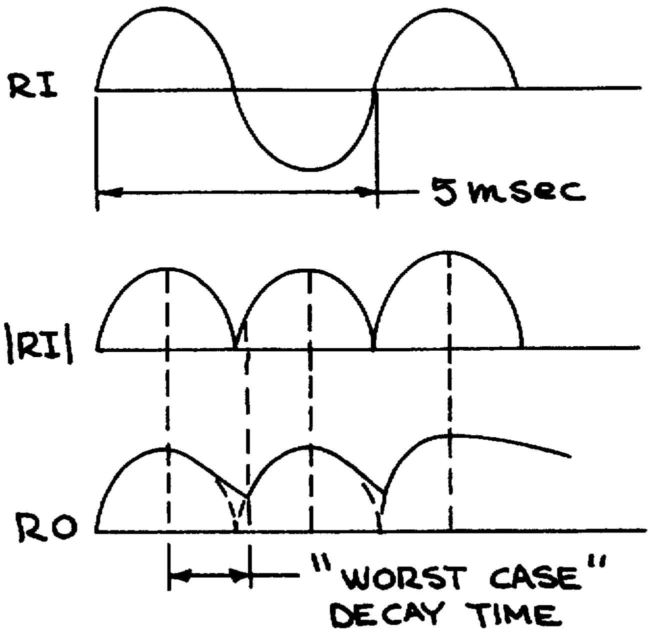
FIG. 7A
FIG. 7B
FIG. 7C

ADAPTIVE NOISE TRANSFORMATION SYSTEM

BACKGROUND OF THE INVENTION

This invention pertains generally to systems for suppressing undesirable noise such as the noise adjacent to freeways arising from vehicular traffic, particularly by transformation of unpleasant noise into sound that is more pleasing to the human ear.

Freeway traffic noise has become a serious public problem in communities having heavily traveled freeways in populated areas, such as the greater Los Angeles area and the San Francisco Bay area. People who live near freeways in these areas are subjected to the constant annoyance of traffic noise, in some cases virtually around the clock. For some time the California Department of Transportation has been attempting to deal with this noise pollution problem by erecting high concrete walls along many freeways. This technique has not been entirely successful. These sound walls decrease the noise level immediately along the freeway, that is, close to the walls, but this noise is still unacceptably unpleasant for many residents in these areas. In some instances it has been found that the walls actually increase the freeway noise level at distances farther away, apparently because of sound reflection and diffraction effects. Furthermore these walls are generally unsightly and block the views from both sides.

Noise suppression is an old problem that has been studied in many different contexts. One technique is to attempt to control the noise at its source. Clearly this is not feasible for traffic noise along a freeway. Passive noise control utilizes absorbers in the sound field. This method is less effective at low frequencies, because it requires large and massive absorbers to obtain effective sound absorption at longer wavelengths. Many practical noise control problems are in fact concerned primarily with suppression of low frequency noise.

Noise "masking" techniques have also been developed, in which unwanted noise is masked by "white noise" generators. This method is discussed in U.S. Pat. No. 4,914,706, issued Apr. 3, 1990 (Krause). This technique is often used in offices and open space buildings to preserve speech privacy, but it is not feasible for the freeway noise problem.

In recent years much research has focused on "active noise control" techniques, in which a secondary sound source is used to generate "anti-noise" in order to cancel the noise by destructive interference of sound waves. This technique was proposed as early as 1936 in a U.S. Pat. No. 2,034,416, issued to P. Lueg. A thorough review of this method is published in the *IEEE Signal Processing Magazine*, October 1993, pages 12–35, in an article entitled "Active Noise Control" by S. J. Elliott and P. A. Nelson. Modern electronic signal processing techniques are fast enough to make active noise control a feasible method for suppression of low frequency noise in some applications. However the noise cancellation technique has fundamental limitations. With a single secondary noise source one can only obtain noise cancellation in a limited spatial region. Eliminating noise in an extended region requires multiple secondary sources. The problem becomes even more complex when the primary source of noise is itself non-localized, as in the case of freeway traffic noise. In short, this method is not a truly effective solution to the freeway noise problem.

SUMMARY OF THE INVENTION

The present technique utilizes a secondary sound source, or "transformation sound" (hereafter termed "TS"), which is combined with the noise from the primary source, or "annoying noise source" (termed "ANS"), to replace the unpleasant noise by a sound that is pleasing to the human ear. It is assumed that there is some replacement sound that is spectrally compatible with the unpleasant noise, and is also more pleasant (or at least less unpleasant) than the noise. In the case of freeway noise, the sound of the ocean surf is pleasant to most people and falls in the same frequency region.

The transformation sound comprises a primary component which is relatively steady, and a plurality of secondary components which are tailored to create a pleasant illusion and are relatively time dependent and appear to the listener to be random. In the case of freeway noise as the ANS, the primary transformation sound (termed "PTS") may be the sound of the surf, and secondary transformation sounds (termed "STS") may include birds chirping, seagull sounds, and so on. The total effect is to transform the ANS noise into a sound that resembles what the listener would hear at a beach.

The transformation sound is generated dynamically by monitoring the ANS sound and adjusting the energy level of the TS so that the valleys in the spectral power density curve of the ANS are filled in with energy from the TS to create the total spectral density of the desired sound, such as the sound at the beach. A microphone detects the ANS noise, and the ANS signal is sent to a control unit, comprising a digital signal processor. The signal is digitized and temporal variations are tracked to generate two tracking signals, a slow tracking signal and a fast tracking signal. The slow tracking signal has a relatively slow response time to fluctuations in the ANS signal, while the fast tracking signal responds rapidly to such fluctuations. The slow tracking signal is utilized to modulate the TS. The difference between the two signals is also monitored, and when this difference exceeds a threshold value (for example, from a very noisy vehicle passing by) the difference signal triggers an STS signal.

The PTS signal is similarly tracked to detect instances when the PTS signal is rapidly decreasing. In such instances the PTS may not be sufficient to adequately transform the ANS, particularly if the ANS happens to be undergoing a sudden increase. When this difference exceeds a threshold value, a second STS signal is generated.

The PTS sounds and STS sounds are stored in a suitable memory in the control unit, and various alternative sounds may be programmed to represent the PTS or STS. Alternatively, the PTS sounds may reside on a CD-ROM and a stream of PTS signals may be continuously fed to the control unit through a CD-ROM player. In other versions of the invention, with a multiple-channel CD-ROM player the STS sounds can be stored on the CD-ROM, or both the PTS and STS sound information can be stored on a hard disk, and in fact there is a substantial variety of storage media that are suitable for the PTS and STS signals.

The PTS and STS signals are combined, and passed through a D/A converter. The analog TS signal is amplified and transmitted to loudspeakers. Alternatively, the signal may be sent to an RF transmitter, and broadcast to a receiver which sends the signals to loudspeakers. The loudspeakers utilize the combined signal to produce a TS in the space where the ANS noise is to be suppressed. The resulting total sound field is pleasing to the ear. For example, in a house located next to a freeway sound wall, a microphone on the exterior wall of the house detects the ANS, and the loudspeakers in the house emit a transformation sound such that persons inside the house hear a sound that gives the impression that the house is located on the beach, rather than next to a freeway.

It is an object of the invention to suppress undesirable noise from an ANS by generating a TS and combining it with the undesirable noise so that the total sound field is pleasing to the ear.

A second object of the invention is to dynamically monitor the ANS and adjust the strength of the TS at each time to the minimum value that is sufficient to transform the ANS to the desirable total sound field.

Another object of the invention is to produce the TS by combining a continuous PTS sound with various STS's so that rapid fluctuations in the ANS noise are transformed by a first STS component of the TS.

Still another object of the invention is to compensate for decreases in the PTS signal by means of a second STS component of the TS.

A further object of the invention is to provide means for the user to select various different sounds for the PTS and STS's.

These and other objects, advantages, characteristics and features of this invention may be better understood by examining the following drawings together with the detailed description of the preferred embodiments.

BRIEF DESCRIPTION OF THE DRAWINGS

FIG. 1 is a basic block diagram of the system according to the present invention.

FIGS. 7A, 7B, and 7C are timing diagrams showing the waveforms at the rectifier shown in FIG. 3.

DETAILED DESCRIPTION OF THE PREFERRED EMBODIMENTS

Figure 2:
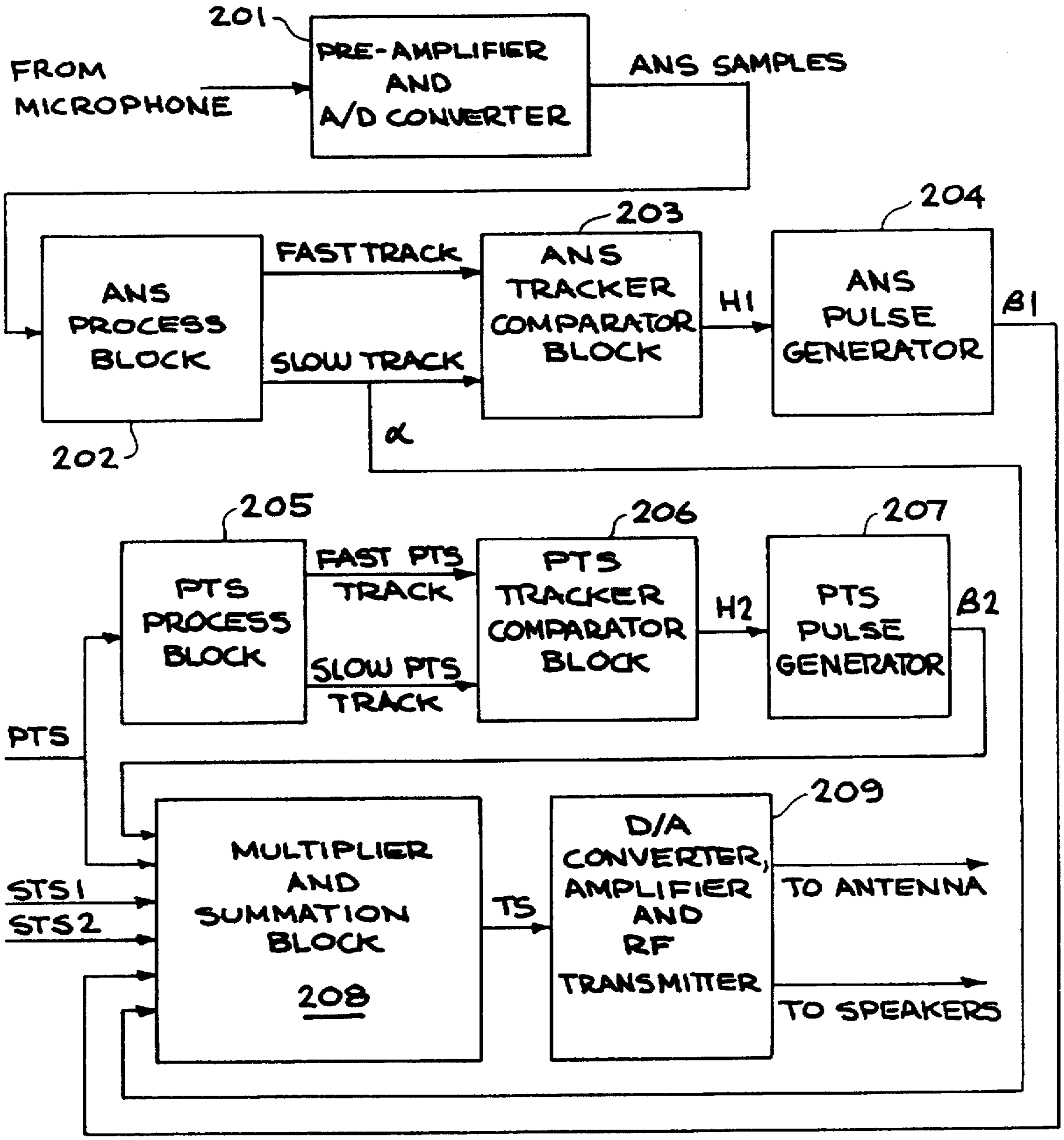
FIG. 2 is a block diagram of the control unit of FIG. 1.

The present invention is especially effective for suppressing traffic noise along a freeway, and the detailed description presented here is for a system designed for this application. Spectrographic analysis of freeway noise samples measured approximately 10 feet from the back side of a freeway sound wall shows that the noise spectrum peaks at approximately 100 Hz, and may have a secondary peak at approximately 1.0 kHz, and the energy above 4.0 kHz is negligible. Similar measurements of the sound of the surf at a California beach show a spectrum that is quite similar to the freeway noise spectrum, and again concentrated in the frequency region below 4.0 kHz. Other beach sounds are not necessarily so similar. For example the spectrum of sound from chirping seagulls falls generally in the region from 3.0 to 5.0 kHz. Thus, the sound of the surf is an appropriate choice for the primary transformation sound (PTS), and the sound of chirping seagulls may be utilized as a secondary transformation sound (STS).

FIG. 1 is a block diagram of the overall system. A microphone 102 located on the exterior wall of a house along a freeway detects unpleasant freeway noise (ANS). The microphone 102 is connected to the control unit 101, which constitutes a digital signal processor (DSP) 103, a storage device 104 for storing the primary and secondary transformation sounds, and a user-operated front panel control 105, coupled together as shown in the Figure. The DSP 103 receives the ANS signal from the microphone 102 and dynamically analyzes the signal. This DSP 103 also receives primary and secondary transformation sound signals from the storage device 104 and switches the STS signals on and off, and modulates the combined PTS and STS signals, in response to the variations in the analyzed ANS signal. The DSP 103 is also connected to a front panel user control unit 105 which allows the user to control the system and includes gain level indicators. The output signal from the DSP 103 is the total transformation sound signal. This signal may be sent through a line out port to an amplifier 106 which feeds into a plurality of loudspeakers. Two loudspeakers 107, 108 are shown in the drawing; however there may be any number of loudspeakers that receive the output of the amplifier 106. These speakers are placed at various locations in the interior of the house. The total sound field in the house produced by the ANS noise and the loudspeaker gives the listener the impression that the house is located at the beach, rather than along a freeway.

FIG. 2 shows the structure of the DSP 103 in FIG. 1. The signal from the microphone 102 passes to a pre-amplifier and A/D converter 201; the output of this unit is a stream of digitized ANS signal samples. These samples are fed into-an ANS process block 202 which tracks the samples and produces two output tracking signals, namely a fast track signal and a slow track signal. Both signals are fed to the ANS tracker comparator block 203. In addition, the slow tracking signal is fed to the multiplier and summation block 208.

The relationship between these signals is illustrated by the timing diagrams shown in FIGS. 5A through 5E. The ANS sample signal undergoes various fluctuations. The fast track signal tracks the energy of the ANS signal with a relatively fast response time, of the order of 5 msec. The slow track signal tracks the energy of the fast track signal in a piecewise linear fashion, and provides substantial smoothing of the signal. The response time of the slow track signal is of the order of 250 msec. The slow track signal can also increase at a much faster rate than it can decrease. From the diagram it will be seen that a sudden fluctuation in the ANS sample signal (such as that caused by a large truck going by on the freeway) can produce a response in the slow track signal with a delay of approximately 250 msec. The fast track signal, however, responds to this fluctuation much more rapidly. The difference between these two signals is thus a measure of the strength of the fluctuation in the ANS sample signal.

Referring again to FIG. 2, the fast track and slow track signals are fed into an ANS tracker comparator block 203, which generates the difference between the fast track signal and (1.5×slow track signal). When this difference is positive, block 203 generates a Boolean logic signal H1 that is "1". Otherwise the signal Hi is a logical "0". This Boolean signal is sent to the ANS pulse generator 204. When-the signal H1 goes to "1" it causes the pulse generator 204 to produce a pulse corresponding to one of the secondary transformation sounds STS1. This pulse signal, designated "β1" in FIG. 5, is sent to the multiplier and summation block 208 and causes the block 208 to receive the secondary transformation signal STS1 samples. The samples comprise a set of sounds that are compatible with the sound of the ocean surf. The length of this pulse β1 is tailored to the particular secondary source, and may be of the order of a second (for the case of chirping birds, for example). At the end of the pulse β1, the input for the secondary source STS1 is disabled. However if the H1 signal is high at this point the ANS pulse generator 204 is re-triggered to produce another logical β1 pulse.

Still referring to FIG. 2, primary transformation sound samples are continuously supplied by the storage device 104 to the multiplier and summation block 208 and the PTS process block 205. This block 205 generates fast and slow tracking signals similarly to the ANS process block 202, "Fast PTS Track" and "Slow PTS Track" respectively. These signals are received by the PTS tracker comparator block 206 and compared in a similar, but reverse, manner to the ANS block 203. Block 203 generates the difference between slow PTS track signal and (1.5×fast PTS track signal). When this difference is positive, block 206 produces a logical pulse H2, which is transmitted to the PTS pulse generator 207. This pulse generator 207 produces a pulse β2 in response, which is transmitted to the multiplier and summation block 208 and actuates the reception of secondary transformation sound samples STS2. These samples are another set of sounds that are compatible with the sound of the ocean surf, such as waves rashing on the beach, bird chirping, etc.

FIGS. 6A through 6E are a set of timing diagrams showing the relationship between the PTS signals and the above pulses. When the PTS signal decreases too rapidly there may be instances when it does not effectively transform the ANS, particularly if the ANS undergoes a spike at the same time. The STS2 signal is introduced to cover these periods. When the falloff occurs, the slow PTS tracking signal will exceed the fast PTS tracking signal by some amount which will cause blocks 206 and 207 to generate the pulses H2and β2, which in turn actuates the STS2 sound. The length of the β2 pulse depends on the nature of the STS2 samples (similarly to the β1 pulse).

Figures 5A, 5B, 5C, 5D, 5E, 6A, 6B, 6C, 6D, 6E:
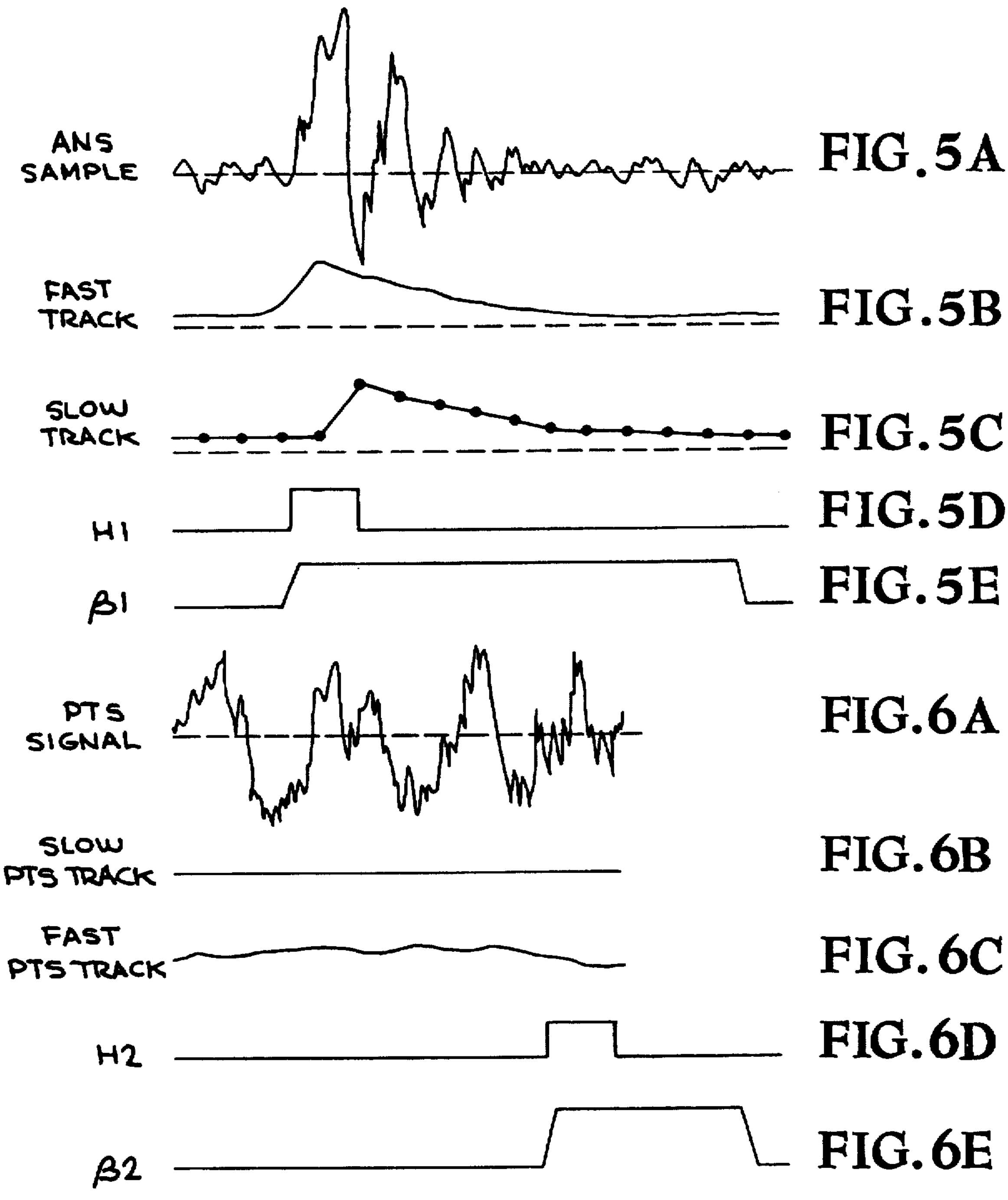
FIGS. 5A, 5B, 5C, 5D, and 5E are timing diagrams showing the ANS tracking signal relationships.
FIGS. 6A, 6B, 6C, 6D, and 6E are timing diagrams showing the PTS tracking signal relationships.

As shown in FIGS. 5E and 6E, the β1 and β2 waveforms have "ramp up" and "ramp down" portions so that the STS signals are smoothly turned on and off. The ramp time is typically of the order of 10 msec. Alternatively this ramping could be included directly in the STS samples themselves, since they only operate intermittently for discrete time periods. Rather than continuously supplying STS signals from the storage device 104, these signals could be fetched in discrete samples according to requests from the DSP 103, and the ramping effect could be incorporated into the samples themselves.

The multiplier and summation block 208 combines the signals PTS, STS1, STS2, β1, β2, and the ANS slow tracking signal designated as α in FIG. 2, to form the total transformation sound signal according to the formula:

$$TS(t)=\alpha(t)\cdot[PTS(t)+\beta 1(t)\cdot STS1(t)+\beta 2(t)\cdot STS2(t)]. \qquad (1)$$

The first term in the brackets of this expression is the primary transformation sound. The second and third terms simply represent turning on and off the secondary transformation sounds as described previously. The sum of these three terms in brackets is scaled by the smoothed tracking signal of the ANS, α(t). Still referring to FIG. 2, this TS signal is sent to the block 209 which includes a D/A converter, amplifier, and optionally an RF transmitter. One output of the block 209 is a direct line to the loudspeakers 107, 108 of FIG. 1. If the block 209 includes an RF transmitter, the TS signal can be fed to the loudspeakers by wireless transmission, through a second output port to the antenna 109.

Figure 3:
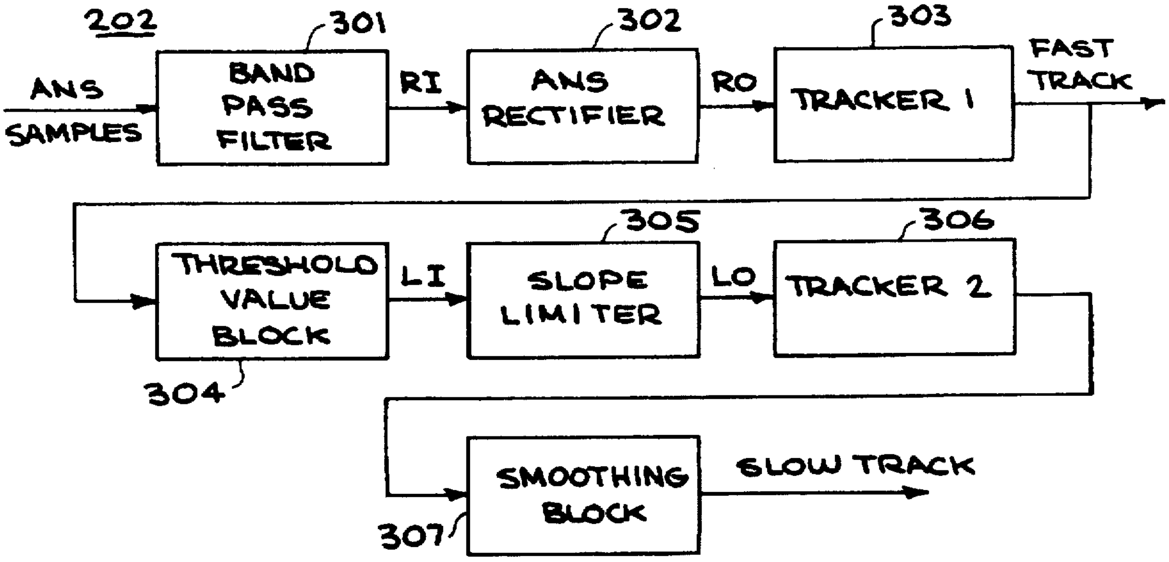
FIG. 3 is a diagram of the ANS process block of FIG. 2.

FIG. 3 shows a block diagram of the ANS process block 202 of FIG. 2. The ANS samples are sent through a band pass filter 301, which filters out frequencies greater than 650 Hz and also removes very low frequencies. The freeway traffic noise is primarily concentrated below 650 Hz. This cutoff frequency makes the device insensitive to most human speech energy that may be present, but still sensitive to vehicle engine and tire noises. Freeway generated energies in the 500 Hz–1.5 kHz range are primarily tire noise, not engine noise. Sounds not arising from the road that are primarily at higher frequencies are thus ignored by this system. The low frequency cutoff is typically approximately 75 Hz, which eliminates many other types of noise, such as wind gusts and door slams. This cutoff also makes the device insensitive to 60-cycle "hum" from the power supply. The filter 301 has been implemented as a 10th order elliptical IIR band pass filter, which exhibits an attenuation in excess of 40 decibels in the frequency range from zero to 60 Hz. The filter has a passband of approximately 75 Hz to 650 Hz.

The output of the bandpass filter 301 drives the ANS rectifier 302, as the input signal RI shown in FIG. 3. The rectifier signal timing relationships are shown in FIGS. 7A through 7C. In principle the output signal of the rectifier 302 is the absolute value of the input signal, |RI|. However, to provide additional smoothing on the rectifier output, the rectifier does not precisely track this variable in the sharp minimum region. The rectifier 302 decay parameter allows a maximum 10% droop at 200 Hz, and was calculated with a "worst case" decay-time of 2.50 msec and at a 27.42857 kHz sample rate.

The rectifier output RO drives the tracker 1 block 303 which produces the fast track ANS signal. The tracker performs a smoothing function on the input wave form. Once each sample period, the tracker generates a fast track output signal that is a linear combination of the input signal and the output signal from the previous cycle. This function can be described by the parameters "a" and "b", which satisfy a+b=1. At sample period "n", the output of tracker 1 is generated according to the algorithm:

$$FT(n)=a\cdot RO(n)+b\cdot FT(n-1), \qquad (2)$$

where FT(n) and RO(n) are the rectifier output signal and the fast track signal at sample period n. The parameter values for this tracker 1 are: a=0.01, b=0.99. These parameters generate the fast track signal described previously.

Referring still to FIG. 3, the fast track signal is transmitted to the threshold value block 304. This circuit imposes a minimum value on the signal to limit the dynamic range of the system to approximately 30 dB. In addition, 1.02 dB of gain is added to the signal. The resulting signal, designated by "LI" in FIG. 3, is fed to the slope limiter 305. This slope limiter imposes a positive and negative slope limitation on the signal. The maximum positive slope is approximately 18 dB/sec, and the maximum negative slope is about −0.50 dB/sec. The positive slope limitation allows door slams and other sudden impulses to be essentially ignored by the system, while the negative slope limitation forces the transformation sound signal to decrease slowly when the ANS signal falls off rapidly. The slope limitations are necessary because sudden variations in the TS signal would result in unnatural sounds and destroy the resemblance to the sound of the surf.

The output of the slope limiter 305, designated "LO" in the drawing, is sent to the tracker 2 block 306. This tracker functions in the same manner as tracker 1 described above. However the "a" and "b" parameter values are chosen to provide far greater smoothing of the signal. For the present implementation these values are: a=0.0002, b=0.9998.

The output of the tracker 2 block 306 is transmitted to the smoothing block 307. This block constructs a piecewise linear approximation for the signal. The resulting signal is linear over sections constituting 1024 sample periods. This smoothing operation eliminates second order terms in the TS signal which would be attenuated versions of the ANS noise samples and would degrade the quality of the resulting transformation sound. The output of the smoothing block 307 is the slow track ANS signal described previously.

Figure 4:
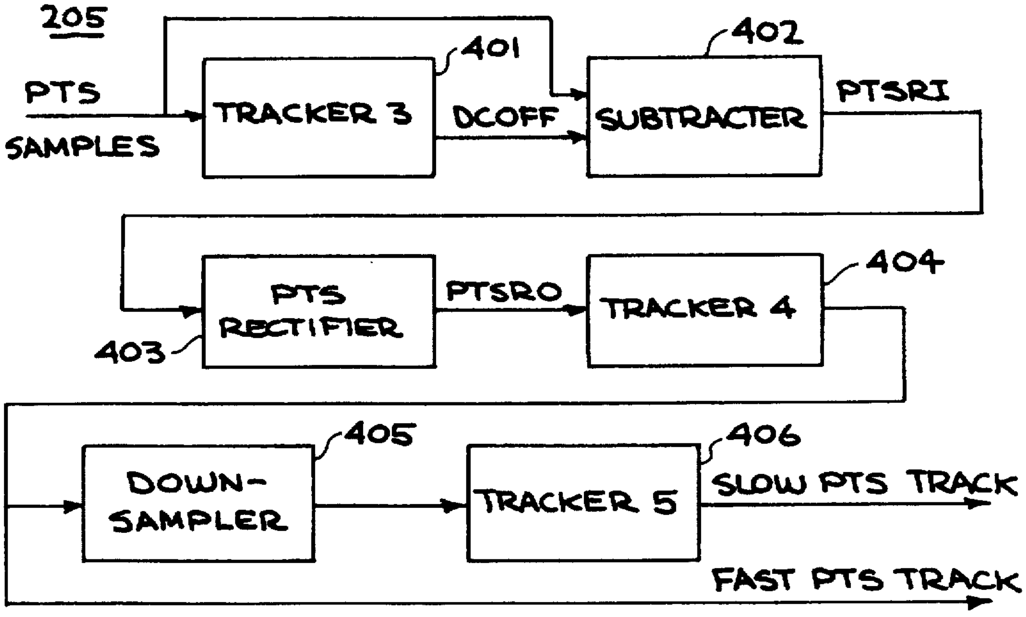
FIG. 4 is a diagram of the PTS process block of FIG. 2.

Referring now to FIG. 4 which shows the structure of the PTS process block 205 of FIG. 2, the PTS samples are input to tracker 3 401 and the subtracter 402, which together remove any DC offset in the PTS sample signals. (These signals are not previously filtered, unlike the above ANS sample signals.) Tracker 3 401 is another "a - b" tracker similar to the previously described trackers. In tracker 3 the parameter values are: a=0.00001, b=0.99999. The resulting output signal, designated "DCOFF" in FIG. 4, is an extremely smoothed track of the PTS sample signal which is essentially the DC component. Both the DCOFF and PTS sample signals are transmitted to the subtracter 402, which creates the difference signal, designated as "PTSRI" in the drawing. This signal is sent to the PTS rectifier 403 shown in FIG. 4. This rectifier is identical in design to the ANS rectifier 302 of FIG. 3.

The output of rectifier 302, designated as "PTSRO" in the figure, is transmitted to tracker 4 404, which performs a tracking operation as previously described with parameter values: a=0.001, b=0.999. The resulting signal is the fast PTS tracking signal described previously.

Still referring to FIG. 4, the fast PTS tracking signal is also input to the downsampler 405, which samples the signal every 1024 sample periods. The downsampled signal is transmitted to tracker 5 406, which runs at a sample rate reduced by a factor of 1024 relative to the rest of the system. For example, if the original sample rate is 27.429 kHz, tracker 5 runs at a sample rate of (27,429 Hz÷1024) =26.8 Hz. Tracker 5 also utilizes a relatively small parameter value for "a" to compute the average PTS signal over a very wide time window of approximately one minute: a=0.0002, b=0.9998. The output signal of this tracker 5 406 is the slow PTS tracking signal described previously.

An important feature of the system is the manner in which the ANS signals detected by the microphone are utilized to control dynamically the magnitude of the transformation sound. As shown in FIG. 2 and Equation (1), the TS is modulated by the ANS slow track signal, designated "$\alpha(t)$". The TS volume broadcast by the loudspeakers should be adjusted to be sufficient to convert the freeway noise to a "surf sound" without being overpowering. Preferably one wants the TS to have the minimum volume to serve this purpose, and typically the requisite volume of the transformation sound is comparable to the volume of the freeway noise.

Of course, the noise volume from a freeway fluctuates in time, and therefore the strength of the TS must be modulated to maintain this function. If one were to modulate the TS with precisely the magnitude of ANS, or even with the fast track ANS signal, the resulting sound would resemble more a replica of the original freeway noise with additional high frequency components from the signal multiplier effects. The ANS slow track signal is designed to provide suitable modulation of the TS without introducing undesirable effects from the ANS noise signal from which it is derived. The limitations on its slope prevent the more rapid ANS variations from creeping into the TS, and the piecewise linearity of $\alpha(t)$ eliminates multiplicative high frequency components from the transformation sound.

The foregoing system has been implemented almost entirely on a Motorola 56002 digital signal processor, with the functions of each component embodied in an assembly language program for this chip. The A/D and D/A conversions are performed by a standard CODEC, and additional analog circuitry is required for the microphone pre-amplifier and the loudspeaker amplifier. As discussed above, a CD player may be used as part of the storage device for the PTS sample sounds. However one can store all of the transformation sound data in a large ROM.

While the above description relates to a system for abating freeway noise, an important advantage of this system is the extreme flexibility in selecting sources for the transformation sound. Any set of compatible pleasing sounds can be utilized for the PTS and STS signals. For example, the transformation sound could be a "storm theme", in which the PTS is the sound of rain and the STS sounds are thunder and wind chimes. Similarly, one could create a "mountain theme" in which the PTS is the sound of a mountain stream and the STS sounds are the sounds of wind and chirping birds. These sounds may all be selected by the user. In addition, because almost the entire system is implemented on a programmable chip, the various parameters governing the signal processing can be easily controlled. As a result, this system may be adapted to suppress a wide variety of unpleasant noises.

Although the system described above utilizes only two secondary transformation sounds, clearly a wider variety of sounds could be incorporated into the system. It is important to make the "repeat rate" of the sound sample sequences as low as possible, so that the listener does not begin to recognize repeating sound patterns. This would destroy the illusion of naturalness. If the PTS is provided by a one-hour compact disk, the CD player replays the disk every hour. However the PTS signal is modulated by the ANS slow track signal before reaching the loudspeakers, so that the effective repeat period is longer than one hour. In addition, the STS sequences are controlled by events in the ANS and occur with no specific periodicity, which also lengthens the effective repeat period. These considerations imply that the degree of perceived randomness, and therefore naturalness, is enhanced by increasing the number of different STS sequences included in the transformation sound.

The foregoing description of a preferred embodiment of the invention and the particular parameters and calculations have been presented for purposes of illustration and description. They are not intended to be exhaustive or to limit the invention to the precise form disclosed, and many modifications and variations are possible in light of the above teaching. This embodiment was chosen and described in order to best explain the principles of the invention and its practical applications to thereby enable others skilled in the art to best utilize the invention in various embodiments and with various modifications as are suitable to the particular use contemplated. It is intended that the spirit and scope of the invention are to be defined by reference to the claims appended hereto.

What is claimed is:

1. A system for suppressing the undesirable effects of a noise source by transforming the noise emitted by the source into replacement sounds in which said effects are alleviated, said system comprising:

detecting means for detecting the noise emitted by said noise source and producing noise signals in response thereto;

storage means for storing a plurality of signals to generate transformation sounds which, when combined with the noise emitted by said noise source, produce replacement sounds in which said effects are alleviated;

processor means communicative with said detecting means and said storage means, said processor means receiving said noise signals from said detecting means and dynamically monitoring said noise signals, said processor means further selecting and receiving transformation sound signals from said storage means in response to said noise signals such that the combination of said noise and the transformation sounds generated by said selected transformation sound signals produces replacement sounds in which said effects are alleviated; and loudspeaker means for emitting said transformation sounds to combine said sounds with said noise, said loudspeaker means being communicative with said processor means, such that said processor means controls said loudspeaker means to cause said transformation sounds to be emitted and combined with said noise.

2. The system according to claim 1, wherein said detecting means comprises a microphone.

3. The system according to claim 1, wherein said storage means comprises a CD-ROM and player.

4. The system according to claim 1, wherein said storage means comprises a ROM.

5. The system according to claim 1, wherein said storage means comprises a hard disk.

6. The system according to claim 1, wherein said processor means includes an RF transmitter, and wherein said loudspeaker means further includes an RF receiver, such that said processor means communicates with said loudspeaker means through said RF transmitter and RF receiver.

7. A system for suppressing the undesirable effects of a noise source by transforming the noise emitted by the source into replacement sounds in which said effects are alleviated, said system comprising:

detecting means for detecting the noise emitted by said noise source and producing noise signals in response thereto;

storage means for storing a plurality of signals to generate transformation sounds which, when combined with the noise emitted by said noise source, produce replacement sounds in which said effects are alleviated, wherein said transformation sounds comprise a primary transformation sound and a plurality of secondary transformation sounds, said primary transformation sound having a spectrum that envelops the spectrum of said noise;

processor means communicative with said detecting means and said storage means, said processor means receiving said noise signals from said detecting means and dynamically monitoring said noise signals, said processor means further selecting and receiving transformation sound signals from said storage means in response to said noise signals such that the combination of said noise and the transformation sounds generated by said selected transformation sound signals produces replacement sounds in which said effects are alleviated;

wherein said processor means selects said primary transformation sound substantially continuously, and wherein said processor means modulates the amplitude of said transformation sounds emitted by said speakers with a filtered signal derived from said noise signals; and loudspeaker means for emitting said transformation sounds to combine said sounds with said noise, said loudspeaker means being communicative with said processor means, such that said processor means controls said loudspeaker means to cause said transformation sounds to be emitted and combined with said noise.

8. The system according to claim 7, wherein said processor selects a first secondary transformation sound for time periods wherein the amplitude of said noise substantially exceeds the amplitude of said primary transformation sound.

9. The system according to claim 8, wherein said processor selects a second secondary transformation sound for time periods wherein the amplitude of said primary transformation sound is decreasing.

10. The system according to claim 7, wherein said processor selects a secondary transformation sound for time periods wherein the amplitude of said primary transformation sound is decreasing.

11. The system according to claim 8, wherein said processor means filters and dynamically tracks said noise signals to produce a first tracking signal with a short response time and a second tracking signal with a long response time, and wherein said processor means selects said first secondary transformation sound by comparing said first tracking signal and said second tracking signal.

12. The system according to claim 11, wherein said filtered signal comprises said second tracking signal.

13. A system for suppressing the undesirable effects of a noise source by transforming the noise emitted by the source into replacement sounds in which said effects are alleviated, said system comprising:

detecting means for detecting the noise emitted by said noise source and producing noise signals in response thereto;

storage means for storing a plurality of signals to generate transformation sounds which, when combined with the noise emitted by said noise source, produce replacement sounds in which said effects are alleviated;

processor means communicative with said detecting means and said storage means, said processor means receiving said noise signals from said detecting means and dynamically monitoring said noise signals, said processor means further selecting and receiving transformation sound signals from said storage means in response to said noise signals such that the combination of said noise and the transformation sounds generated by said selected transformation sound signals produces replacement sounds in which said effects are alleviated; and loudspeaker means for emitting said transformation sounds to combine said sounds with said noise, said loudspeaker means being communicative with said processor means, such that said processor means controls said loudspeaker means to cause said transformation sounds to be emitted and combined with said noise;

wherein said noise source comprises a freeway having vehicular traffic which emits said noise, and wherein said transformation sounds comprise the sound of ocean surf.

14. A method for suppressing the undesirable effects of noise emitted by a noise source by transforming the noise into replacement sounds in which said effects are alleviated, said method comprising the steps of:

detecting the noise to form a noise signal;

selecting a transformation sound in response to said noise signal which, when combined with said noise produces a replacement sound in which said undesirable effects are alleviated; and combining said transformation sound with said noise to produce said replacement sound;

wherein the step of selecting a transformation sound further comprises the steps of:

selecting a first transformation sound having a spectrum that envelops the spectrum of said noise;

combining said first transformation sound substantially continuously with said noise;

dynamically monitoring said noise signal to detect sudden increases in the volume of said noise;

selecting a second transformation sound; and combining said second transformation sound with said noise and said first transformation sound during periods of said sudden increases in said noise volume.

15. The method according to claim 14, further comprising the steps of:

selecting a third transformation sound; and combining said third transformation sound with said noise and said first and second transformation sounds during periods when said first transformation sound is decreasing in volume.

* * * * *